(12) United States Patent
Ono et al.

(10) Patent No.: US 7,833,552 B2
(45) Date of Patent: Nov. 16, 2010

(54) XANTHOHUMOL-ENRICHED HOP EXTRACT

(75) Inventors: Mitsunori Ono, Lexington, MA (US); Naoto Yamaguchi, Bethesda, MD (US)

(73) Assignee: Flaxan GmbH & Co. KG, Nurnberg (DE)

( * ) Notice: Subject to any disclaimer, the term of this patent is extended or adjusted under 35 U.S.C. 154(b) by 120 days.

(21) Appl. No.: 12/190,965

(22) Filed: Aug. 13, 2008

(65) Prior Publication Data
US 2009/0124703 A1 May 14, 2009

Related U.S. Application Data

(60) Provisional application No. 60/955,906, filed on Aug. 15, 2007.

(51) Int. Cl.
*A01N 65/00* (2009.01)
(52) U.S. Cl. .................................................... 424/725
(58) Field of Classification Search ....................... None
See application file for complete search history.

(56) References Cited

U.S. PATENT DOCUMENTS

| 3,892,808 | A | 7/1975 | Mitchell |
| 6,867,332 | B1 | 3/2005 | Biendl et al. |
| 2004/0121040 | A1 | 6/2004 | Forster et al. |
| 2005/0019438 | A1 | 1/2005 | Bourges-Sevenier et al. |
| 2005/0042318 | A1 | 2/2005 | Erdelmeier et al. |

FOREIGN PATENT DOCUMENTS

EP    1543834    6/2005

OTHER PUBLICATIONS

International Search Report issued in International Application No. PCT/US2008/073013, Feb. 16, 2009.
International Preliminary Report on Patentability for related PCT Application PCT/US2008/073013, mailed Feb. 25, 2010.

*Primary Examiner*—Michael V Meller
(74) *Attorney, Agent, or Firm*—Edwards Angell Palmer & Dodge LLP; Jeffrey D. Hsi; Melissa Hunter-Ensor, Esq.

(57) ABSTRACT

A method for preparing a xanthohumol-rich hop composition. The method includes providing a solution that contains xanthohumol-containing hop substances and effecting precipitation of non-xanthohumol hop substances by adjusting both the salt concentration and pH value of the solution. The xanthohumol-rich hop composition prepared by this method can be used for treating various diseases, e.g., skin disorders, and bacterial infection.

14 Claims, No Drawings

XANTHOHUMOL-ENRICHED HOP EXTRACT

CROSS-REFERENCE TO RELATED APPLICATION PARAGRAPH

This application claims the benefit of U.S. Provisional Application No. 60/955,906 filed on Aug. 15, 2007. The contents of which, is hereby incorporated by reference in its entirety.

BACKGROUND

Xanthohumol exists in hops, which are primarily used in brewery. As a strong antioxidant, it exhibits benefits in treating diseases associated with oxidative stress, e.g., cancer and neurodegenerative disorder.

A number of methods have been developed to prepare xanthohumol-containing hop extracts for medical uses. These methods, however, have several disadvantages. For example, hop extracts prepared by hitherto known methods contain a substantial amount of iso-xanthohumol, which is undesirable for its estrogen activity, or chlorophyll, which is undesirable for its green color. As another example, when supercritical $CO_2$ extraction is used, expensive facilities are required so as to reduce the danger of explosion.

Given the above disadvantages, it is highly desirable to develop a safe and inexpensive method for preparing from hops xanthohumol-rich compositions that contain little iso-xanthohumol and chlorophyll.

SUMMARY

This invention is based on an unexpected discovery that adjustment to certain salt concentrations and pH values of xanthohumol-containing solutions prepared from hops substantially salts out non-xanthohumol substances and thus enriching xanthohumol.

Accordingly, in one aspect, the present invention features a method of preparing from hops a composition having a high xanthohumol content. This method includes at least five steps: (1) providing a first solution containing hop substances that include 0.4-90% (e.g., 0.4-20%) by weight xanthohumol and a solvent that includes up to 90% by volume water and at least 3% by volume a water miscible solvent; (2) adjusting the salt concentration of the first solution to 0.05-5.0 M (e.g., 0.5-2.5 M) and its pH value to 9.5-13 (e.g., 10.5-12.0) to effect formation of a first precipitate; (3) removing the first precipitate to obtain a second solution; (4) adjusting the pH of the second solution to 3-9 (e.g., 7-8) to effect formation of a second precipitate; and (5) collecting the second precipitate that contains 40-95% by weight xanthohumol.

In this method, the first solution can be prepared by extracting raw hops (i.e., hop cones or hop flowers) or spent hops with a polar organic solvent, removing (completely or partially) the polar organic solvent to obtain a residue or a concentrated hop extract, and then dissolving the residue or the extract in another solvent, which can be water, a water miscible solvent, or a mixture thereof.

The first solution thus prepared or prepared by other methods is then subjected to adjustment of its salt concentration and pH to salt out non-xanthohumol substances, i.e., step (2). Adjustment of the salt concentration can be achieved by mixing the first solution with an aqueous salt solution. The pH value can be adjusted by adding to it a basic solution, e.g., NaOH or KOH. Step (4) also requires pH adjustment, which can be achieved with an acidic solution.

In one implementation of this method, salting-out is performed twice instead of once. See steps (2) and (4) below. This implementation includes at least the following seven steps: (1) providing a first solution containing hop substances that include 0.4-90% (0.4-20%) by weight xanthohumol and a solvent that includes up to 90% by volume water and at least 3% by volume a water miscible solvent; (2) adjusting the salt concentration of the first solution to 0.05-0.3 M to effect formation of a first precipitate; (3) removing the first precipitate to obtain a second solution; (4) adjusting the salt concentration of the second solution to 0.3-5.0 M and its pH to 9.5-13 to effect formation of a second precipitate; (5) removing the second precipitate to obtain a third solution; (6) adjusting the pH value of the third solution to 3-9 to effect formation of a third precipitate; and (7) collecting the third precipitate that contains 40-95% by weight xanthohumol.

In another aspect, this invention provides a composition containing at least 30% (e.g., 50% or 75%) by weight xanthohumol and 0.4-4.5% (e.g., 0.4-3.5%, 0.4-3.0%, 0.4-2.5%, or 0.4-1.5%) by weight isoxanthohumol. In one example, this composition is prepared by any of the methods described above.

Any of the xanthohumol-enriched compositions described above can be used for treating disease/disorder such as skin disorder, inflammatory disease, cancer, viral or bacterial infection, diabetes, obesity, and high cholesterol levels. To achieve the intended therapeutic effects, an effective amount of the composition is administered to a subject in need thereof. The term "treating" as used herein refers to the application or administration of a composition including one or more active agents to a subject, who has one of the diseases/disorders mentioned above, a symptom of the disease/disorder, or a predisposition toward the disease/disorder, with the purpose to cure, heal, alleviate, relieve, alter, remedy, ameliorate, improve, or affect the disease/disorder, the symptoms of the disease/disorder, or the predisposition toward the disease/disorder. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with another active agent.

Also within the scope of this invention is use of any of the xanthohumol-enriched compositions described herein for the manufacture of a medicament for the just-mentioned treatments.

The details of one or more embodiments of the invention are set forth in the description below. Other features, objects, and advantages of the invention will be apparent from the description and from the claims.

DETAILED DESCRIPTION

The starting material for the method of this invention, i.e., a xanthohumol-containing solution (hereinafter "first solution"), can be prepared from xanthohumol-containing hop materials, e.g., hop cones, hop flowers, and spent hops. This solution contains a solvent such as water, a water miscible solvent, or a mixture thereof and hop substances including 0.5-90% by weight xanthohumol. The concentration of xanthohumol in the first solution can be 3% (w/v) or lower.

In one example, the first solution is prepared by extracting a xanthohumol-containing hop material with a water miscible solvent (e.g., ethanol or acetone). More specifically, the hop material is soaked in the water miscible solvent under a suitable temperature (e.g., 50° C.) for a sufficient period of time (e.g., 30 minutes) until xanthohumol is fully dissolved. The first solution is obtained by removing, e.g., via centrifugation or filtration, insoluble hop substances, and, optionally, removing part of the water miscible solvent such that the volume of the first solution is manageable.

In another example, the first solution is prepared as follows. A hop material, e.g., spent hops, is extracted with a polar organic solvent to produce a solution containing the organic solvent and hop substances dissolved therein. The polar organic solvent is an organic solvent having a polarity greater than that of ether. Exemplary polar organic solvents include, but are not limited to, ethanol, methanol, ethyl acetate, or acetone. Subsequently, the polar organic solvent is removed from the solution, e.g., by evaporation, to afford a dry or semi-dry hop extract, which can contain 0.4-20% by weight xanthohumol. If the polar organic solvent is a water miscible solvent, e.g., ethanol, the solvent can be only partially removed from the solution to afford a concentrated hop extract. The hop extract is then dissolved in water, a water miscible solvent, or a mixture thereof. The mixture can contain at least 3% (e.g., 10%, 50%, or 90%) by volume a water miscible solvent and up to 90% (e.g., 50%) by volume water. The ratio of water and the water miscible solvent in the mixture can be determined based on the amount of xanthohumol to be dissolved therein. Exemplary water miscible solvents include methanol, ethanol, propanol, butanol, pentanol, acetone, tetrahydrofuran, dimethylformamide, dimethylamine, and dimethyl sulfoxide.

The first solution can also be prepared by dissolving, in water, a water miscible solvent, or a mixture thereof, a hop extract prepared by the method of the invention. In other words, a product prepared by this method can be subjected to the same method again to further enrich xanthohumol. Alternatively, the first solution can be prepared by dissolving, in water, a water miscible solvent, or a mixture thereof, a hop extract prepared by methods known in the art, e.g., supercritical $CO_2$ extraction (see US Patent Application 2004/0121040).

The first solution is then subjected to adjustment of its salt concentration and pH value to salt out non-xanthohumol substances. To adjust its salt concentration to 0.05 M to 5.0 M (e.g., 0.2-2.5 M or 0.5-1.0 M), the first solution can be mixed with an aqueous salt solution. The salt solution can contain either an inorganic salt (e.g., KCl, LiCl, NaCl, NaBr, KBr, LiBr, KI, LiI, CaSO4, MgSO4, and a quarterly ammonium salt), or an organic salt (e.g., citric acid salt, tartaric acid salt, and acetic acid salt). To adjust its pH to 9.5-13, a suitable amount of a basic solution (e.g., NaOH or KOH) is added to the first solution. The order of salt concentration adjustment and pH adjustment is inconsequential. The mixture thus formed can then be kept under 4-40° C. for a sufficient period of time to allow salting-out of non-xanthohumol hop substances (e.g., chlorophyll, chlorophyll derivatives, and hop oily resins). After removing the salted-out substances, the pH value of the resultant solution is re-adjusted to 3-9 (e.g., 5-9 or 7-8), using, for example, an acidic solution such as HCl or $H_2SO_4$. The solution can be stirred slowly under 4-40° C. for a certain period of time (e.g., 30 minutes) to facilitate precipitation of xanthohumol. The precipitate thus formed is then collected and dried under vacuum. The resultant powder contains 40-95% by weight xanthohumol.

Optionally, the first solution mentioned above is first mixed with an aqueous salt solution to reach a salt concentration of 0.05 M to 0.3 M. Under this condition, hop substances such as chlorophyll are considerably salted out. After removing these substances, the resultant solution is subjected to the same steps as described above.

The xanthohumol-containing hop powder prepared by the method described above can be used for treating oxidative stress-associated medical conditions, such as cancer (e.g., breast, prostate, colon, and ovarian), aging, atherosclerosis, ischemic injury, inflammation, and neurodegenerative diseases (e.g., Parkinson's and Alzheimer's).

The hop powder described above also can be used for treating skin disorders, e.g., acne, rosacea, exzema, psoriasis, atopic dermatitis, contact dermatitis, seborrhea, sunburn, and skin aging. Without being bound by theory, xanthohumol, an active agent contained in the hop powder described herein, exerts its therapeutic effects in treating a skin disorder via the following two mechanisms: (1) xanthohumol quenches singlet oxygen, which causes or aggravates various skin disorders, e.g., acne, atopic dermatitis, and skin aging; and (2) xanthohumol inhibits growth of various gram positive bacteria, which is involved in development of acne and other skin diseases.

In addition, the xanthohumol-enriched hop powder is effective in treating inflammatory disease. An inflammatory disease is characterized by local or systemic, acute or chronic inflammation. Examples include retinopathy, inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease or ILD, idiopathic pulmonary fibrosis, and ILD-associated with rheumatoid arthritis), asthma, and allergic rhinitis.

Moreover, the xanthohumol-enriched hop powder described herein is effective in treating diabetes (both type I and type II), obesity, viral infection, and bacterial infection, and is also effective in lowering plasma cholesterol levels in a subject.

To be used in any of the above-mentioned treatments, the hop powder can be mixed with a pharmaceutically acceptable carrier, and optionally with another therapeutically active agent, to form a pharmaceutical composition. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of the xanthohumol-containing pharmaceutical composition. Examples of other carriers include colloidal silicon oxide, magnesium stearate, cellulose, sodium lauryl sulfate, D&C Yellow # 10, microcrystalline cellulose, mannitol, glucose, defatted milk powder, polyvinylpyrrolidone, and starch, or a combination thereof. This pharmaceutical composition can then be presented in a variety of forms, such as tablet, capsule, powder, or liquid.

The xanthohumol-containing pharmaceutical composition can be administered to a subject in need of the treatment via suitable routes, e.g., oral administration, once or multiple times per day or administered once every several days. A solid formulation for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microglycolate, and alginic acid. Tablet binders that can be used include acacia, methylcellulose, sodium carboxymethylcellulose, polyvinylpyrrolidone (Povidone3), hydroxypropyl methylcellulose, sucrose, starch, and ethyl-cellulose. Lubricants that can be used include magnesium stearates, stearic acid, silicone fluid, talc, waxes, oils, and colloidal silica.

This solid formulation can be designed such that the composition is released in the intestine. For example, the composition is confined in a solid sub-unit or a capsule compartment that have respectively a matrix or a wall or a closure comprising an enteric polymer which dissolves or disperses at the pH of the small or large intestine to release the drug substance in the intestine.

In another example, the xanthohumol-containing hop powder is a component of a food product (e.g., yogurt, milk, or soy milk) or a food supplement (e.g., a nutrient supply or an herbal product). Such food products can be prepared by methods well known in the food industry.

When targeting a skin disorder, the xanthohumol-enriched hop powder described herein is preferred to be formulated in a manner suitable for topical administration, e.g., as a liquid and semi-liquid preparation that can be absorbed by the skin. Examples of a liquid and semi-liquid preparation include, but are not limited to, topical solutions, liniments, lotions, creams, ointments, pastes, gels, and emugels.

Topical solutions are homogeneous mixtures prepared by dissolving one or more active agents in a solvent. The solutions may contain other cosmeceutically acceptable chemicals to buffer, stabilize, or preserve the active agent(s). Solvents commonly used for preparation of topical solutions include ethanol, water, glycerol, and propylene glycol. Optionally, L-menthol can be added to a topical solution.

Lotions, preferably used for treating a large body area, are typically liquid or semiliquid preparations in which solid particles, including an active agent, are present in a water or alcohol base. They are usually suspensions of solids, and preferably, contain a liquid oily emulsion of the oil-in-water type. The insoluble matter in a lotion should be finely divided such that it applies to the skin surface without friction. Lotions typically contain suspending agents to produce better dispersions as well as compounds useful for localizing and holding the active agent(s) in contact with the skin, e.g., methylcellulose, sodium carbozymethyl-cellulose, or the like.

Creams are viscous liquid or semisolid emulsions, either oil-in-water or water-in-oil, containing cream bases. Cream bases are water-washable and contain an oil phase, an emulsifier, and an aqueous phase. The oil phase, also called the "internal phase," is generally comprised of petrolatum and a fatty alcohol such as cetyl or stearyl alcohol. The aqueous phase usually, although not necessary, exceeds the oil phase in volume, and contains a humectant. The emulsifier in a cream formulation can be a nonionic, anionic, cationic, or amphoteric surfactant. Exemplary surfactants include sorbitan esters or polyoxyethylene derivatives thereof (e.g., polyoxyethylene fatty acid esters) and carboxypolymethylene derivatives (e.g., carbopol).

Ointments are semisolid preparations that are typically based on petrolatum or other petroleum derivatives. Ointment bases should possess emolliency or other desirable features. As with other carriers or vehicles, they are preferably inert, stable, nonirritating, and nonsensitizing. There are four types of suitable ointment bases: oleaginous bases, emulsifiable bases, emulsion bases, and water-soluble bases. See Remington: The Science and Practice of Pharmacy, 19$^{th}$ Ed., at pages 1399 and 1404. Oleaginous ointment bases include, for example, vegetable oils, fats obtained from animals, and semisolid hydrocarbons obtained from petroleum. Emusifiable ointment bases, also known as absorbent ointment bases, contain little or no water and include, for example, hydroxystearin sulfate, anhydrous lanolin, and hydrophilic petrolatum. Emulsion ointment bases are either water-in-oil emulsions or oil-in-water emulsions, and include, but are not limited to, cetyl alcohol, glyceryl monostearate, lanolin, and stearic acid. Preferred water-soluble ointment bases are prepared from polyethylene glycols of varying molecular weights.

Pastes are semisolid dosage forms in which an active agent(s) is suspended in a suitable base. Depending on the nature of the base, pastes are divided between fatty pastes and those made from single-phase aqueous gels. The base in a fatty paste can be petrolatum, hydrophilic petrolatum, or the like. The pastes made from single-phase aqueous gels generally incorporate carboxymethylcellulose or the like as a base.

Gels and emugels both include a commonly known gel forming agent, such as cellulose derivatives (e.g., methyl cellulose, hydroxyethyl cellulose, and carboxymethyl cellulose), vinyl polymers (e.g., polyvinyl alcohols and polyvinyl pyrrolidones), carboxypoly-methylene derivatives (e.g., carbopol), pectins and gums (e.g., gum arabic and tragacanth, alginate, carrageenate, agar, or gelatin). The gel or emugel formulations may further contain an auxiliary agent commonly known in the art, such as a preservative, a stabilizer, a colorant, or a perfume.

The xanthohumol-containing topical formulations described above can further include one or more other active agents, such as a vitamin (e.g., vitamin B, 1,25-dihydroxy vitamin D3, vitamin K, vitamin A, and vitamin C), an antimicrobial agent (e.g., tolnaftate, ketoconazole, erythromycin, and tetracycline), an insect-repellent (e.g., aliphatic, cyclic or aromatic amides, citronella oil, terpineol, cineole, neem oil, and ethyl butyacetylaminopropionate), a self-tanning agent (e.g., dihydroacetone and lawsone), an anti-inflammatory agent (e.g., hydrocortisone, prednisone, prednisolone, aspirin, aloe vera, and mixtures thereof), a topical analgesic (e.g., lidocaine, benzocaine, butacaine, and clove oil), a skin redness reducer (e.g., guanidine derivatives and L-arginine derivatives).

Without further elaboration, it is believed that the above description has adequately enabled the present invention. The following examples are, therefore, to be construed as merely illustrative, and not limitative of the remainder of the disclosure in any way whatsoever. All publications cited herein are incorporated by reference.

EXAMPLE 1

Preparing a Xanthohumol-Rich Dry Hop Composition from Spent Hops Extracted Initially with Ethyl Acetate 1.45 kg spent hops from *Hallertau Hallertauer* were extracted with ethyl acetate, resulting in 82.6 g of a dark-green waxy crude hop extract after removal of the solvent. HPLC analysis showed that this crude hop extract contained 9.9 g xanthohumol, i.e., 12% by weight. The crude extract was dissolved in 1.5 L ethanol to generate an ethanol solution. 0.83 L NaCl (0.2 M) was then added to the ethanol solution to effect formation of a dark green oily precipitate, which was removed. The supernatant thus obtained was first mixed with a sufficient amount of NaOH such that its pH value reached 11.0. It was subsequently mixed with 2.5 L water and 1.0 L NaCl (2.75 M), resulting in the formation of a brown-colored precipitate. An orange-colored supernatant, obtained by filtering out the precipitate, was then produced. The pH value of this supernatant was adjusted to 8.0 with a sufficient amount of 25% $H_2SO_4$. A yellow precipitate thus formed was collected by filtration. The recovered precipitate was then dried under vacuum, resulting in yellow powder (11.3 g). HPLC analysis showed that the powder contained 66% by weight xanthohumol and 1.8% by weight iso-xanthohumol. No chlorophyll was detected in the yellow powder.

EXAMPLE 2

Preparing a Xanthohumol-Rich Dry Hop Composition from Spent Hops Extracted Initially with Acetone 200 g spent hops (containing 1.6 g xanthohumol, i.e., 0.8% by weight) from *Hallertau Hallertauer* were ground and extracted with 1.0 L acetone for 2 hours at 50° C. with overhead mixer agitation. The resultant extract was then filtered with a Buchner funnel and the residues were washed with 200 ml of acetone two times. The filtrates were collected and concentrated under vacuum at 50° C. to reach a total volume of about 60 ml. The concentrated extract was then mixed with 70 ml water and the solution thus formed was subjected to concentration under the same conditions to generate an acetone-free solution (70 ml). This solution was mixed with 130 ml ethanol and the resultant mixture was stirred at 50° C. for 30 minutes to ensure that all xanthohumol contained in the solution was completely dissolved. Subsequently, the solution was mixed with a suitable amount of 12 N NaOH gradually until its pH reached 11. Then, the solution was mixed with 320 ml water and 19.4 g KCl. After readjusting its pH to 11, the resultant mixture was subjected to filtration to remove the precipitate contained therein. The filtrate was collected, mixed with an appropriate amount of 25% $H_2SO_4$ to reach a pH value of 8.0, and then stirred very slowly for 30 minutes to effect formation of a yellow precipitate. This precipitate was collected by filtration, washed with about 30 ml water, and dried under vacuum at 50° C. for about 16 hours. The resultant powder, 2.522 g, contained 1.299 g xanthohumol (51.5% by weight). The overall yield of xanthohumol was 81%.

As shown below, the water solubility of the xanthohumol contained in the powder prepared by the method described above is much higher than the xanthohumol contained in hop compositions prepared by conventional methods.

The following three samples were suspended in water (1 mg xanthohumol/ml) to form three mixtures:

Sample 1: a xanthohumol-rich composition prepared by $CO_2$ extraction (containing 30% by weight xanthohumol);

Sample 2: a xanthonumol-rich composition prepared by silica gel chromatography (containing 98% by weight xanthohumol), and Sample 3: the powder described above in this Example, (containing 50% by weight xanthohumol)

After being sonicated for 5 minutes, the three mixtures were centrifuged at 3,000 rpm for 2 minutes or 12,000 rpm for 3 minutes. The supernatants thus formed were collected. 100 µl of each supernant were diluted with methanol, and then injected into HPLC to determine xanthohumol concentrations under the following conditions:

| HPLC system: | LC1100 series with Diode Array Detector (Agilent); |
|---|---|
| Mobile phase A: | 10 ml of 1M Triethylammonium acetate (TEAA) buffer (pH 7, #90357, Fluka) mixed with 990 ml of HPLC grade water (OmniSolv, EMD Chemicals); |
| Mobile phase B: | 10 ml of 1M TEAA buffer (pH 7, #90357, Fluka) mixed with 990 ml of HPLC grade acetonitrile (OmmniSolv, EMD Chemicals); |
| Column: | C18 end capped column 4.6 × 250 mm, 5 um (Capcell Pak C18 SG, Shiseido); |
| Column temperature: | 35° C. |
| Injection volume: | 20 uL |
| Flow rate: | 1 ml/min |
| Linear gradient: | from 30% B at 0 min to 90% B at 20 min and hold 90% B for 5 min |
| Read-out wavelength: | 370 nm |

The results thus obtained are shown in Table 1 below:

TABLE 1

Water Solubility of Xanthohumol Contained in Different Hop Compositions

| | Xanthohumol content (% by weight) | Solubility (µm, 3000 rpm) | Solubility (µm, 12000 rpm) |
|---|---|---|---|
| Sample 1 | 30 | 2.3 | 0.86 |
| Sample 2 | 98 | 6.0 | 2.3 |
| Sample 3 | 50 | 12.5 | 6.6 |

Clearly, the xanthohumol contained in Sample 3 (prepared by the method described above) has a significant high water solubility relative to the xanthohumol contained in hop compositions prepared by conventional $CO_2$ extraction or silica gel chromatography.

Further, the conversion of xanthohumol to isoxanthohumol in the following samples were tested:

Sample A: the hop powder prepared by the method described in this example.

Sample B: Sample 1 described above dissolved in cremophor EL (obtained from Sigma Chemical Co., St. Louis, Mo.) to form a solution with a xanthohumol concentration of 1% (w/v). See US Patent Application 2007/0248549.

Sample C: Sample 1 described above dissolved in cremophor EL to form a solution with a xanthohumol concentration of 4% (w/v). See US Patent Application 2007/0248549.

Samples A, B, and C were incubated at 75° C. for 120 hours and the content ratios between isoxanthohumol and xanthohumol in these samples were determined via HPLC before and after incubation and the ratios of isoxanthohumol/xanthohumol (IX/XN) were calculated.

The ratio of IX/XN is 0.03 in all of the three samples before the incubation. After the incubation, IX/XN of Sample A increased slightly to 0.04, indicating that only a small amount of xanthohumol was converted to isoxanthohumol during the incubation. Differently, the post-incubation IX/XN ratios of Samples B and C increased significantly to 0.2 and 0.3 respectively, indicating that a large amount of xanthohumol in each of the two samples was converted to isoxanthohumol during incubation. These results demonstrate that the xanthohumol contained in the hop composition prepared by the method of this invention is much more stable than that contained in hop compositions prepared by traditional methods.

OTHER EMBODIMENTS

All of the features disclosed in this specification may be combined in any combination. Each feature disclosed in this specification may be replaced by an alternative feature serv-

What is claimed is:

1. A method of preparing from hops a composition having a high xanthohumol content, the method comprising:
   providing a first solution containing hop substances and a first solvent, wherein the hop substances include 0.4-20% by weight xanthohumol and the first solvent includes up to 90% by volume water and at least 3% by volume a water miscible solvent;
   adjusting the salt concentration of the first solution to 0.05 M to 5.0 M and the pH value of the first solution to 10.5-12.0 to effect formation of a first precipitate;
   removing the first precipitate to obtain a second solution;
   adjusting the pH of the second solution to 7-8 to effect formation of a second precipitate; and
   collecting the second precipitate, wherein the second precipitate contains 40-95% by weight xanthohumol.

2. The method of claim 1, wherein the first solution is prepared by extracting hops or spent hops with a second solvent, removing the second solvent to obtain a residue, and dissolving the residue in the first solvent; wherein the second solvent is a polar organic solvent.

3. The method of claim 1, wherein the water miscible solvent is selected from the group consisting of methanol, ethanol, propanol, butanol, pentanol, acetone, tetrahydrofuran, dimethylformamide, dimethylamine, and dimethyl sulfoxide.

4. The method of claim 3, wherein the water miscible solvent is ethanol.

5. The method of claim 1, wherein the salt concentration of the first solution is adjusted by mixing it with an aqueous solution containing an inorganic salt selected from the group consisting of KCl, NaCl, $CaSO_4$, and $MgSO_4$.

6. The method of claim 1, wherein the salt concentration of the first solution is adjusted by mixing it with an aqueous solution containing an organic salt selected from the group consisting of citric acid salt, tartaric acid salt, and acetic acid salt.

7. The method of claim 1, wherein the salt concentration of the first solution is adjusted to 0.2-2.5 M.

8. A method of preparing a high xanthohumol content composition from hops, the method comprising:
   providing a first solution containing hop substances and a first solvent, wherein the hop substances include 0.4-20% by weight xanthohumol and the first solvent includes up to 90% water by volume and at least 10% by volume a water miscible solvent;
   adjusting the salt concentration of the first solution to 0.05 M to 0.3 M to effect formation of a first precipitate;
   removing the first precipitate to obtain a second solution;
   adjusting the salt concentration of the second solution to greater than 0.3 M to 5.0 M and the pH value of the second solution to 10.5 to 12.0 to effect formation of a second precipitate;
   removing the second precipitate to obtain a third solution;
   adjusting the pH of the third solution to 7-8 to effect formation of a third precipitate; and
   collecting the third precipitate, wherein the third precipitate contains xanthohumol 40-95% by weight.

9. The method of claim 8, wherein the first solution is prepared by extracting hops or spent hops with a second solvent, removing the second solvent to obtain a residue, and dissolving the residue in the first solvent; wherein the second solvent is a polar organic solvent.

10. The method of claim 8, wherein the water miscible solvent is selected from the group consisting of methanol, ethanol, propanol, butanol, pentanol, acetone, tetrahydrofuran, dimethylformamide, dimethylamine, and dimethyl sulfoxide.

11. The method of claim 10, wherein the water miscible solvent is ethanol.

12. The method of claim 8, wherein the salt concentrations of the first and second solutions are adjusted by mixing them with an aqueous solution containing an inorganic salt selected from the group consisting of KCl, NaCl, $CaSO_4$, or $MgSO_4$.

13. The method of claim 8, wherein the salt concentrations of the first and second solutions are adjusted by mixing them with an aqueous solution containing an organic salt selected from the group consisting of citric acid salt, tartaric acid salt, and acetic acid salt.

14. The method of claim 8, wherein the salt concentration of the second solution is adjusted to 0.5-2.5 M.

* * * * *